United States Patent
Ahn et al.

(10) Patent No.: US 9,089,437 B2
(45) Date of Patent: Jul. 28, 2015

(54) FUSION DEVICE, SYSTEMS AND METHODS THEREOF

(75) Inventors: Edward S. Ahn, Dover, MA (US); John Cvinar, Highland Beach, FL (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 1831 days.

(21) Appl. No.: 12/445,936

(22) PCT Filed: Oct. 16, 2007

(86) PCT No.: PCT/US2007/081559
§ 371 (c)(1),
(2), (4) Date: Sep. 28, 2010

(87) PCT Pub. No.: WO2008/140551
PCT Pub. Date: Nov. 20, 2008

(65) Prior Publication Data
US 2011/0004307 A1    Jan. 6, 2011

Related U.S. Application Data

(60) Provisional application No. 60/851,972, filed on Oct. 16, 2006.

(51) Int. Cl.
| | | |
|---|---|---|
| A61F 2/44 | (2006.01) | |
| A61B 17/70 | (2006.01) | |
| A61F 2/28 | (2006.01) | |
| A61F 2/30 | (2006.01) | |
| A61F 2/46 | (2006.01) | |

(52) U.S. Cl.
CPC .............. *A61F 2/441* (2013.01); *A61F 2/4455* (2013.01); *A61B 17/7098* (2013.01); *A61F 2/28* (2013.01); *A61F 2/447* (2013.01); *A61F 2/4465* (2013.01); *A61F 2002/2817* (2013.01); *A61F 2002/2835* (2013.01); *A61F 2002/302* (2013.01); *A61F 2002/30062* (2013.01); *A61F 2002/30225* (2013.01); *A61F 2002/30579* (2013.01); *A61F 2002/30583* (2013.01); *A61F 2002/30586* (2013.01); *A61F 2002/30772* (2013.01); *A61F 2002/30904* (2013.01); *A61F 2002/4495* (2013.01); *A61F 2002/4631* (2013.01); *A61F 2210/0004* (2013.01); *A61F 2210/0085* (2013.01); *A61F 2230/0065* (2013.01); *A61F 2230/0069* (2013.01); *A61F 2310/00011* (2013.01); *A61F 2310/00179* (2013.01); *A61F 2310/00293* (2013.01); *A61F 2310/00353* (2013.01)

(58) Field of Classification Search
USPC ............................................ 623/17.11–17.16
See application file for complete search history.

(56) References Cited

U.S. PATENT DOCUMENTS

| | | |
|---|---|---|
| 5,549,679 A | 8/1996 | Kuslich |
| 2005/0049707 A1 | 3/2005 | Ferree |
| 2007/0055275 A1* | 3/2007 | Schaller .................. 606/92 |

FOREIGN PATENT DOCUMENTS

| | | |
|---|---|---|
| EP | 1 132 061 | 9/2001 |
| EP | 1 212 992 | 6/2002 |
| WO | 03/099171 | 3/2003 |
| WO | 2005/071190 | 8/2005 |
| WO | 2005102226 | 11/2005 |

* cited by examiner

*Primary Examiner* — Sameh Boles
(74) *Attorney, Agent, or Firm* — Fitch, Even, Tabin & Flannery LLP (57) ABSTRACT

The invention provides a fusion device for use in spinal fusion procedures. The invention also provides systems and methods that include filling the fusion device with a cement composition.

26 Claims, 5 Drawing Sheets

FUSION DEVICE, SYSTEMS AND METHODS THEREOF

CROSS-REFERENCE TO RELATED APPLICATIONS

This application is a U.S. national phase application filed under 35 U.S.C. §371 of International Application PCT/US07/81559, filed on Oct. 16, 2007, designating the United States, which claims the benefit of U.S. Provisional Application No. 60/851,972, filed on Oct. 16, 2006, which are hereby incorporated by reference herein in their entirety.

FIELD OF THE INVENTION

The invention relates to spinal fusion implant devices for fusing adjacent vertebrae and, in particular, to implant devices positionable in the intervertebral space and fixed in place using a cement composition.

BACKGROUND OF INVENTION

The spine principally includes a series of vertebrae and spinal discs located in a space between adjacent vertebrae. The vertebrae are formed of hard bone while the discs comprise a comparatively soft annulus and nucleus. The discs support the vertebrae in proper position and enable the torso to be rotated and to bend laterally and anteriorly-posteriorly. The discs also act as shock absorbers or cushions when the spine is experiencing shock, such as during running or jumping.

A variety of spinal conditions result in a person experiencing pain or limited physical activity and ability. More specifically, damage to vertebrae composing the spine and spinal discs between the vertebrae may occur as a result of trauma, deformity, disease, or other degenerative conditions. Some of these conditions can be life-threatening, while others cause impingement on the spinal cord resulting in pain and a lack of mobility. Removing the impingement, thus reducing swelling or pressure from the damaged or diseased tissue against the spinal cord, can relieve the pain and often promotes healing and return of normal nervous system functioning. However, the absence of proper medical care may lead to further damage and degeneration of spinal health and to permanent spinal cord damage.

Damage to the spine often results in reduced physiological capability. For instance, damage to the disc or vertebra may allow the annulus to bulge, commonly referred to as a herniated disc. In more severe cases, the damage may allow the nucleus to leak from the annulus. In any event, such damage often causes the vertebrae to shift closer or compress, and often causes a portion of the disc to press against the spinal cord.

One manner of treating these conditions is through immobilization of the vertebrae in a portion of the spine, such as two or more adjacent vertebrae, which is often beneficial in reducing or eliminating pain. Immobilization and/or fusion have been performed via a number of techniques and devices, and the type of injury often suggests a preferred treatment regime.

One form of immobilization is known as spinal fusion surgery, in which two or more adjacent or consecutive vertebrae are initially immobilized relative to each other and, over time, become fused in a desired spatial relationship. For instance, rigid rods or plates may be attached to the spine to immobilize the spine for a sufficient length of time to allow fusion between the vertebrae and the intervertebral implant to take place and/or to allow boney ingrowth into the disc space. Desirably the vertebrae are relatively immobilized at the proper intervertebral distance, replicating the support characteristics of the healthy spine. An implant spacer may be placed between the vertebrae, which over time will fuse to both adjacent vertebrae or be entirely resorbed and replaced with bony growth.

Spinal fusion surgery substantially reduces or eliminates the motion between vertebral segments, which thereby alleviates a source of pain in some patients. Although fusion treatments sacrifice rotation and flexion between the affected vertebrae such that some loss of movement and flexibility of the spine is experienced, the non-fused portions of the spine are largely able to compensate for most normal movement expected by a patient. Furthermore, the compression on the spinal cord due to the injury is reduced or eliminated, and the fused vertebrae protect the spinal cord from injury. The spinal fusion surgery can also be used to prevent or impede progressive deformity of the spine in some patients. Subjects in need of spinal fusion include those suffering from fractured vertebra, spondylolisthesis, protrusion or degeneration of the spinal disc, abnormal curvature of the spine (such as scoliosis or kyphosis), spinal tumor, spinal infection, or spinal instability.

Currently, a number of fusion devices are known. Implantation of such devices may involve excavating a portion of one or both adjacent vertebrae to provide a volume for locating the device therein. Many fusion devices have surface features such as anchor members in the form of prongs, teeth, spikes, and the like, which extend away from upper and lower surfaces of the device for being embedded into the adjacent vertebrae. In order to locate the device within the intervertebral space, instruments may be used to spread the vertebrae apart.

Some fusion devices are made from bio-resorbable materials, such as natural bone, hydroxyapatite, calcium phosphates, and other bone-like compositions Fusion devices comprising bio-resorbable materials can be integrated into adjacent bone over time eventually providing a single solid mass of bone, however devices prepared using such materials tend to have relatively weak compressive strengths.

Stronger materials, such as polyetheretherketones (PEEK), may be used to manufacture fusion devices to provide increased strength. Surface features such as spikes and teeth made of such materials can penetrate vertebral bone to secure the device thereto. However, these stronger materials are not bio-resorbable.

The purpose of the fusion procedure is to develop a lattice, matrix, or solid mass of bone joined with and extending between the adjacent vertebrae and through the intervertebral space. Eventually, the formed or developed bone and the vertebrae are joined to provide a somewhat unitary, incompressible structure that maintains the proper pre-fusion spatial relationship for the size to reduce or eliminate the impingement on the spinal cord. Accordingly implants formed of these stronger materials are left as a redundant structure which is unable to be absorbed by the body or replaced by bone growth and which acts as a boundary interface between the implant device and any resultant bone growth. While the effect of the boundary interface can be addressed by reducing the size of the implant so that more graft material can be packed into the intervertebral space around the implant, this can result in less secure implantation.

Accordingly, there is a need for improved spinal fusion systems and for improved methods for performing spinal fusion surgery. There is also a need for implants that are compatible with body chemistry and physiology and that possess mechanical stability for hardness, compressive strength, flexural strength, and/or wear resistance, as well as controlled microstructure to develop functional gradients, controlled interfacial properties to maintain structural integrity in physiological conditions, and/or surface chemistry tailored to provide appropriate adhesion properties, chemical resistance, and lasting patient comfort.

The present invention may be used to fulfill these, as well as other needs and objectives, as will be apparent from the following description of embodiments of the present invention.

SUMMARY OF THE INVENTION

The invention provides for a device, systems and methods for fusing adjacent vertebral bodies. The device of the invention is variously referenced herein as the "implant," "fusion implant," "fusion device," or "spinal fusion device" of the invention.

The spinal fusion device of the invention is implanted within an intervertebral space between adjacent upper and lower vertebrae and secured to the vertebrae with cement. The fusion device comprises a body having upper and lower endplate facing surfaces for contacting adjacent vertebrae, with one or more sidewalls formed therebetween. The fusion device includes upper and lower endplate facing surfaces each having at least one opening for delivering cement material to adjacent contact surfaces of the vertebrae above and below the implant. Utilizing quick-setting cement compositions with the device can allow for almost immediate fusion of the vertebrae, thus, reducing or eliminating the need for adjuvant fixation devices such as screws, plates, and/or rods, while also simultaneously providing precise delivery of cement to contact surfaces between the fusion device and vertebrae.

The openings in the spinal fusion device's upper and lower endplate facing surfaces are positioned and configured so that cement is directed only toward the vertebral surfaces in contact with the device, which prevents cement from escaping into the adjacent vertebral space, where it could cause potential injury by bonding to nerve tissue or other nearby tissues, or harden into sharp fragments that may damage said tissues. Eventually, the openings may also provide a pathway for bone from the adjacent vertebrae to grow into and fuse with the device.

The spinal fusion device of the invention may optionally include one or more fill ports, such as one or more injection ports, configured to externally receive a cement material from a delivery device, such as a syringe or any other injection device. The fill port may be connected to one or more channels that lead to one or more openings through the exterior of the spinal fusion device. The spinal fusion device may also contain a hollow core that is a cavity for receiving cement from the fill port, with the cavity either leading directly to openings in the exterior of the implant or connected to one or more channels that lead to such openings. Generally, a syringe is used to dispense the cement material into the spinal fusion device using sufficient pressure so as to substantially fill the channel(s) and/or the hollow core and force the cement through the openings in the upper and lower endplate facing surfaces to contact the adjacent vertebrae. The fill port is preferably positioned on a lateral sidewall between the endplate facing surfaces so as to allow the implant to be injected with cement subsequent to insertion of the implant into the intervertebral space, but the fill port may also be used for cement injection prior to insertion of the implant into the intervertebral space, if desired.

Fusion of the adjacent vertebrae is enhanced by injection of cement material into the spinal fusion device before and/or after insertion of the implant into the intervertebral space. The cement polymerizes in situ and either binds the spinal fusion device to the surface of or interdigitates into the endplate cortical bone and the exposed cancellous bone in the upper and lower vertebral bodies. The cement material polymerizes to fuse the implant to the upper and/or lower vertebral bodies. By injecting the cement material into the implant and subsequently forcing the cement to emanate outward from the implant to the vertebral surfaces that are in direct contact with the implant, a more precise application of cement is achieved than when cement is applied to the exterior of the vertebra and/or implant before or during implantation. The resulting continuous uniform cement connection between the vertebrae facilitates bone ingrowth and more secure fusion.

The body of the spinal fusion device may be formed as a rigid structure with lateral sidewall surfaces that are impermeable to the cement and discrete openings through upper and lower endplate facing surfaces. A rigid spinal fusion device can be formed of any suitable load bearing, biocompatible material. Suitable materials include bioceramic materials, metal, inert polymers such as PEEK, resorbable polymers, resorbable polymer composites, bone grafts, and the like.

Alternatively, the spinal fusion device may be made of flexible material that may be rolled or otherwise flexed and compacted to minimize volume for purposes of insertion and subsequently inflated with cement subsequent to insertion into the intervertebral space. Flexible spinal fusion devices may be made, for instance, of a mesh comprising of woven fibers or sheets of polyethylene, Teflon®, polyesters, lycra, nylon, rayon, cellulose, collagen and the like. More preferably, the flexible implant comprises resorbable sheets or polymers, such as those made of polyglycolic acid, polylactic acid, polyglycolic/co-lactic acid polymers, polyurethanes, polyaryl carbonates, polytyrosine carbonates, polycaprolactones, polydioxanes, polyphosphazenes, polybutyric acids, polyvaleric acids, and the like. The structure of such a flexible mesh can form a selectively permeable surface through which cement is released to contact adjacent bone. In such cases, an impermeable cement barrier layer can be added to those surfaces of the device that will not contact the adjacent vertebrae, so that the release of cement is focused toward bone-contacting surfaces. Alternatively, or in addition, discrete openings may be provided through the flexible material to direct cement to adjacent vertebral surfaces.

Any biocompatible cement composition may be used with the spinal fusion device, but preferred cements may be selected according to various parameters, especially setting time, binding strength, and flow characteristics. In addition it is preferred that the setting reaction of the cement is not exothermic, so that possible damage to adjacent tissues is minimized or eliminated. The cement preferably sets within minutes with a low exotherm and has a strength sufficient to adequately support the spine and simultaneously immobilize the implant and adjacent vertebrae. The viscosity of the cement when freshly mixed and injected into the implant should preferably allow the cement to flow out of the implant and into contact with the vertebrae in a controlled manner. Preferred cements will also be radiopaque, will rapidly set and cure, will maintain physiological pH and be biocompatible. Preferred cements include those described in co-pending U.S. patent application Ser. No. 11/500,798, which published as U.S. 20070032568 A1, and U.S. Provisional Application No. 60/968,462, both of which are specifically incorporated by reference as if fully set forth herein. Other cements may also be used, such as cements based on the polymerizable acrylate resin polymethylmethacrylate (PMMA), calcium phosphate cements, glass ionomer cements, and the like. The cement may also further comprise filler materials such as inert fillers or bioactive components that promote bone growth. Each component of the cement product can also, optionally, include additional materials.

In another aspect, the invention provides a system for fusing adjacent upper and lower vertebrae using a spinal fusion implant device of the invention. The device is sized to fit in the intervertebral space between adjacent vertebrae and having a body in which a flow path is formed that has an inlet and which opens to an outlet or outlets that face at least one, and preferably both, of the adjacent vertebrae. Injectable cement can be injected through the inlet into the flow path and, thereby, directed to the upper and lower vertebra through the corresponding facing opening of the implant body.

The system further includes injectable cement material with predetermined rapid setting characteristic so that setting of the cement fixes the implant body to the vertebrae in the intervertebral space. In addition, upon injection the preferred cement material has a viscosity that provides the cement material with desired flow characteristics through the flow path prior to setting. In certain embodiments, the system can further include a delivery device adapted to deliver the injectable cement material to the inlet of the implant body. The flow path and delivery device are configured so that the flow of the cement material is provided with sufficient pressure to generate flow of the cement through the flow path from the inlet of the body to the outlet or outlets so that the cement material sets substantially at the time it engages along the corresponding vertebra and prior to flowing beyond the implant body in the intervertebral space.

In the methods of the invention, spinal fixation and stability are maintained or enhanced by inserting the fusion device between two adjacent vertebral bodies and injecting cement into one or more hollow cores in the fusion device. The injected cement fills the one or more hollow cores and contacts the surface of one or more adjacent vertebral bodies and, in some methods, interdigitates into the cancellous bone in the vertebral bodies, thereby achieving substantially immediate fixation and/or mechanical stability. By using cement to achieve mechanical stability, the invention can minimize or eliminate the need for additional fixation appliances, such as the pedicle rods and screws. Moreover, the invention can advantageously provide a uniform, homogenous connection between opposing vertebra to facilitate bony ingrowth.

Thus, in certain embodiments, the fusion device of the invention is used in a standalone application that does not include the use of adjuvant fixation. In alternate embodiments, the fusion device can be used in conjunction with adjuvant fixation.

DETAILED DESCRIPTION

The spinal fusion device of the invention is used to maintain disc height between two adjacent vertebral bodies while bone forms between the two vertebrae. The device permits injection of cement into one or more hollow cores in the fusion device. The cement fills the one or more hollow cores and engages the vertebral body surfaces located on one or both sides of the implanted device. Once the cement has set, independent motion of the vertebrae is substantially or wholly eliminated. The device, systems and methods of the invention provide for reduced time for fixation and improved stability of the vertebral motion segment, thereby reducing or eliminating the need for adjuvant fixation. By reducing or eliminating the drilling, tapping or insertion of screws associated with adjuvant fixation, the invention provides for shorter spinal fusion procedures. In some embodiments, as boney spinal fusion occurs, the cement will resorb and act as a continuous scaffold for tissue ingrowth without the use any bone growth enhancement devices such as autograft material. In additional embodiments, the device further includes graft compartment into which autograft or other bone graft material can be placed.

The spinal fusion device of the invention can have any suitable shape and comprise any suitable biocompatible material. Suitable shapes include, for example, shapes that are substantially a cylinder, a ring, a disc, a rectangle, a U-shape, a boomerang or the like that are sized for cervical, thoracic, or lumbar use. Suitable biocompatible materials include metal, plastic, resorbable polymers, resorbable polymer composites, bone graft material, and the like.

Exemplary suitable materials for use in a rigid spinal fusion device of the invention include polyetheretherketones (PEEK), PEEK-calcium phosphate composites, PEEK-bone graft composites, hydroxyapatite, tricalcium phosphate, 316 stainless steel, duralloy, cobalt-cobalt chrome, titanium alloy such as Ti6Al4V alloys, polymers, plastic, resorbable polymers (i.e. polyglycolic acid, polylactic acid, poly glycolic-co-lactic acid, polydioxane, polycaprolactoner), other resorbable polymer composites with calcium phosphates, allografts, bone grafts, and the like. In preferred embodiments, the rigid fusion device comprises densified or consolidated hydroxyapatite or tricalcium phosphate, in particular nanocrystalline materials as described in U.S. Pat. No. 6,013, 591, reissued as RE 39,196, and U.S. patent application Ser. No. 10/635,402, which published as U.S. 2005/0031704 A1, the entire contents of all three of which are specifically incorporated by reference herein. In a more preferred, embodiment, the fusion device is made from nanocrystalline calcium phosphate NanOss™ (Angstrom Medica, Woburn, Mass.). Such a device is especially useful in the methods described herein, used in conjunction with injectable NanOss IsoF-LEX™ Cement (Angstrom Medica, Woburn, Mass.).

The implants of the invention desirably have a resorption time of about 1 year or more (e.g., about 3 years or more, about 6 years or more, or about 10 years or more). The rate of resorption will depend at least in part on the crystal size as well as the composition of the implant. Smaller crystal sizes will be resorbed more rapidly than larger crystal sizes. The desired resorption rate will depend on the application and the crystal size and composition can be tailored to match a desired resorption rate.

Figure 1:
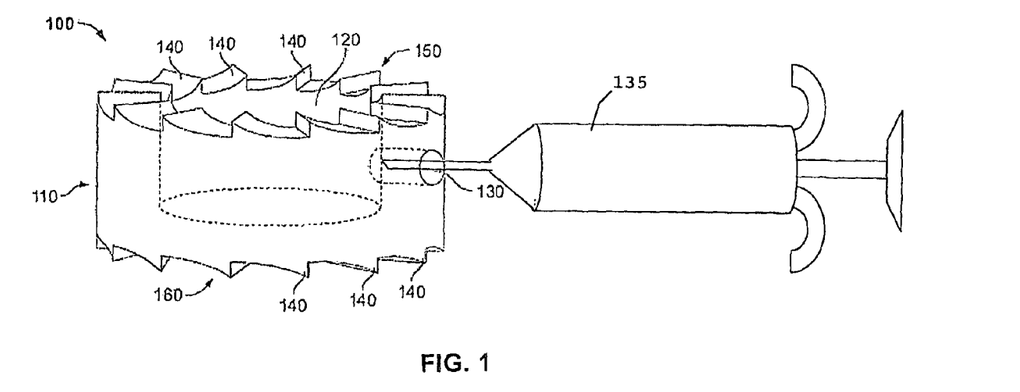
FIG. 1 is a perspective view of a fusion device of the invention

FIG. 1 illustrates a spinal fusion device 100 of the invention, which can be inserted into the intervertebral space between upper and lower adjacent vertebrae during spinal fusion surgery. The outer surface 110, 150, 160 of the device 100 includes a sidewall 110, which extends generally between an upper endplate facing surface 150 and a lower endplate facing surface 160. Preferably, the upper endplate and lower endplate facing surfaces 150, 160 include teeth structures 140, which engage the vertebral surfaces directly above and below the device 100 to thereby resist dislocation within and/or expulsion from the intervertebral space. The sidewall surface 110 includes a fill port 130. Fixation and stability of the adjacent vertebrae is enhanced by (i) inserting the implant 100 into an intervertebral space so that the upper and lower endplate facing surfaces 150, 160 contact the adjacent vertebral surfaces that are above and below the intervertabral space, respectively, and (ii) using an injection delivery device 135 to inject cement material through fill port 130 into hollow core 120 until cement fills the hollow core 120 and is directed through openings in the upper and lower endplate facing surfaces 150, 160 of the device to the vertebral surfaces that are, respectively, directly above and below the device 100. After injection, the cement material sets, quickly fusing the device 100 to the upper and lower vertebrae.

Figure 9:
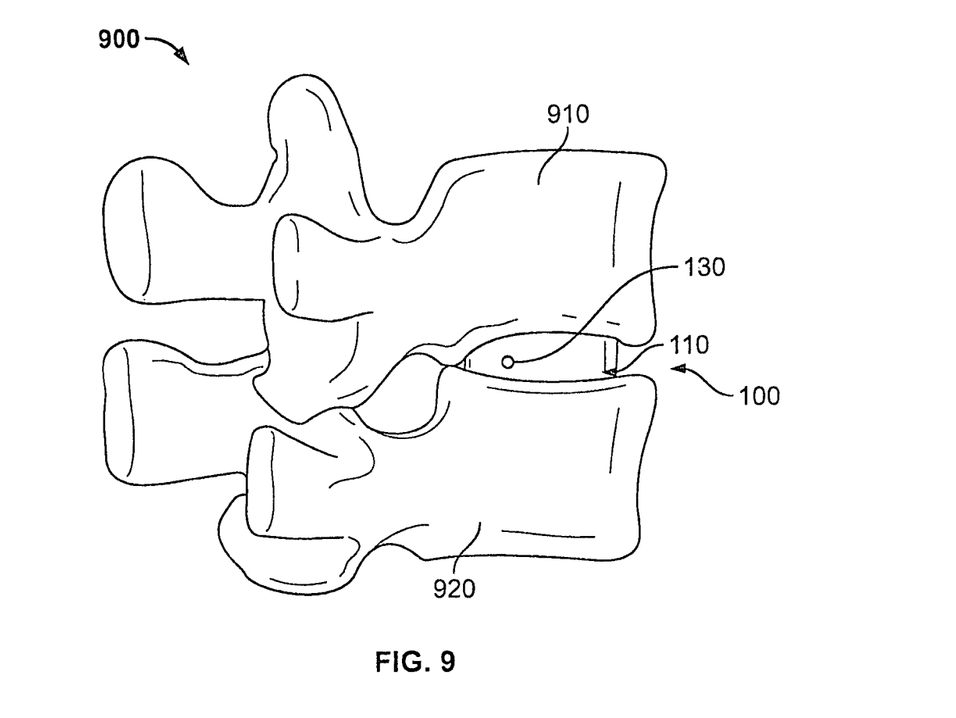
FIG. 9 is a side view of a fusion device of the invention between a superior and an inferior vertebra.

FIG. 9 illustrates a spinal fusion device 100 of the invention disposed within the intervertebral space between an upper vertebra 910 and a lower vertebra 920. The sidewall 110 of the device includes a filler port 130 for injection of cement. The filler port 130 is depicted as being positioned close to the posterior lateral location of the spinal segment 910, 920. Generally, the devices of the invention are preferably positioned within the intervertebral space so that the filler port (or more generally, the portion of the device for receiving cement) is located at or near the point of insertion of the device into the intervertebral space. Such positioning facilitates delivery of cement to the device via the same surgical access used to insert the device.

In another aspect, the spinal fusion implant includes a graft compartment for receiving bone graft material. The term bone graft material is used herein to refer to biological additives such as orthobiologics that promote bone replacement. Thus, bone graft material can include allografts, autografts, demineralized bone matrix, collagen, growth factors, and/or bone morphogenic proteins.

Figure 2:
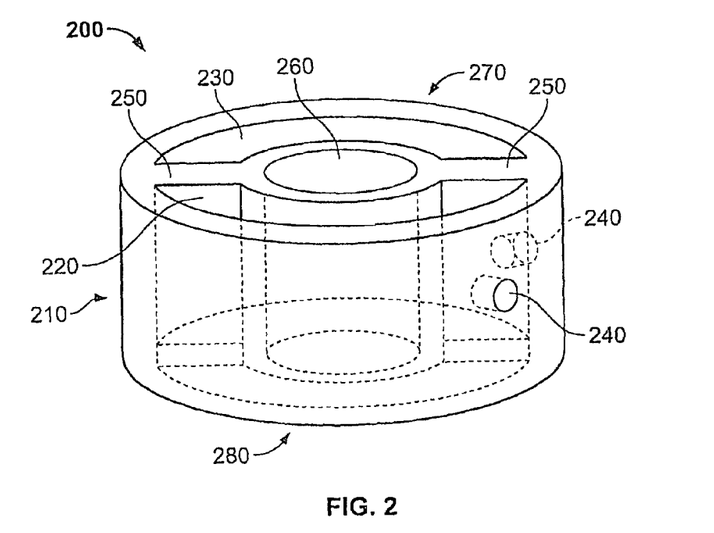
FIG. 2 is a perspective view of a fusion device of the invention with two hollow cores for cement and a graft compartment.

FIG. 2 illustrates a spinal fusion device 200 with a graft compartment 260 and two hollow cores 220, 230, each of which extends from the upper endplate facing surface 270 to the lower endplate facing surface 280. One or more internal walls 250 separate the hollow cores 220, 230 from each other and from the graft compartment 260. Upon insertion of the device 200 into the intervertebral space between adjacent vertebra, cement material can be independently injected into each of the two fill ports 240 in the sidewall 210, to thereby independently control injection pressure, the amount of cement material, and/or the type of cement that is injected into each of the hollow cores 220, 230 and that subsequently contacts each of the vertebral surfaces, respectively, which are directly above and below the device 300. In further embodiments, the upper and lower endplate facing surfaces 270, 280 can include teeth structures (such as those illustrated in FIG. 1) to resist dislocation within and/or expulsion from the intervertebral space.

Figure 3:
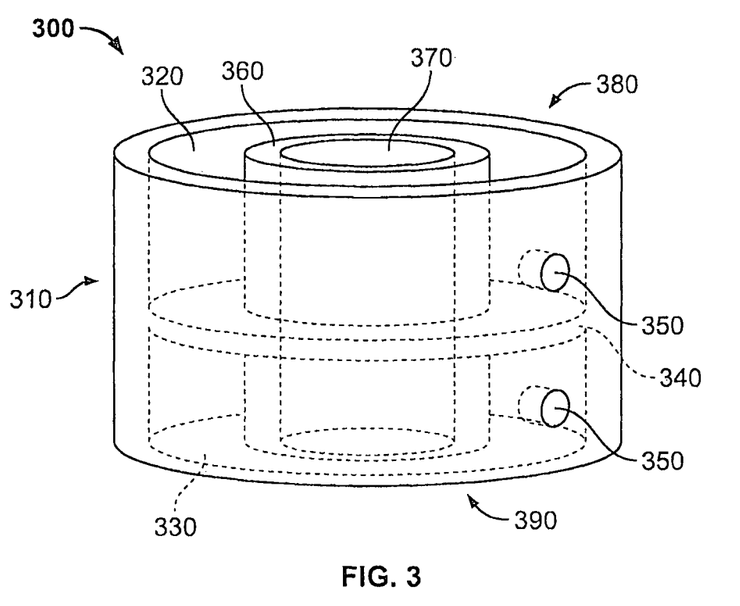
FIG. 3 is a perspective view of a fusion device of the invention with upper and lower hollow cores for cement as well as a graft compartment.

FIG. 3 illustrates a spinal fusion device 300 of the invention that includes upper and lower hollow cores 320, 330, which direct injected cement material to the upper and lower endplate facing surfaces 380, 390, respectively. The implant 300 includes a midline internal wall 340, which separates the hollow cores 320, 330, and at least two fill ports 350 in the sidewall 310. Thus, the device provides for the independent control of injection pressure, the amount of cement, and/or the type of cement that is injected into each of the upper and lower hollow cores 320, 330 and that subsequently contacts each of the vertebral surfaces, respectively, which are directly above and below the device 300. Additionally, as illustrated in FIG. 3, the implant 300 includes a graft compartment 370, which extends from the upper endplate facing surface 380 to the lower endplate facing surface 390 and which is separated from the hollow cores 320, 330 by an internal wall 360. In further embodiments, the upper endplate and lower endplate facing surfaces 380, 390 can include teeth structures (such as those illustrated in FIG. 1) to resist dislocation within and/or expulsion from the intervertebral space.

When cement is added to one or more hollow cores that generally surround one or more graft compartments (such as the generally concentric arrangement of hollow core(s) around a graft compartment illustrated in FIGS. 2, 3, 7, and 8), the spinal fusion device of the invention advantageously provides a cement barrier that prevents the migration of loose bone chips or other graft material from the implant graft compartment, which can result in irritation or other damage to surrounding vertebral tissues.

Figure 4:
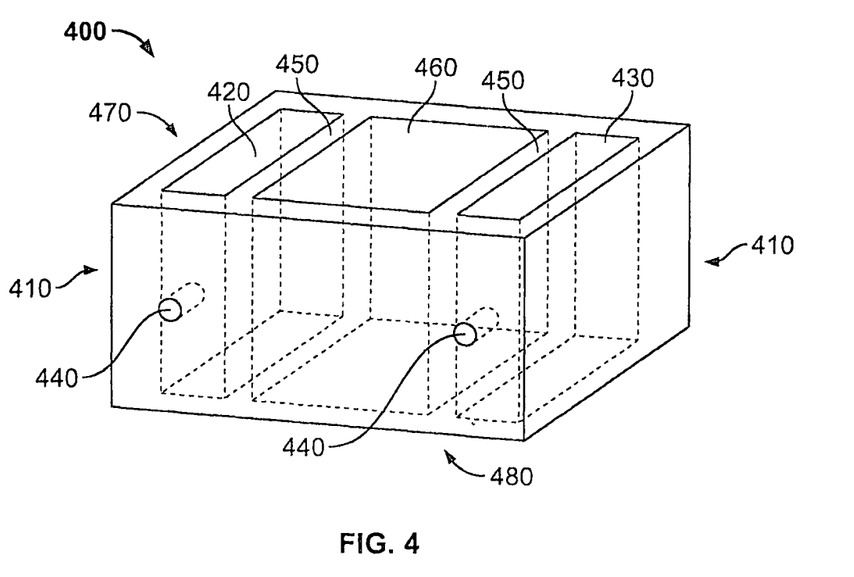
FIG. 4 is a perspective view of a fusion device of the invention with two hollow cores for cement and a graft compartment.

FIG. 4 illustrates a spinal fusion device 400 according to the invention. The device 400 has a sidewall 410 that generally extends between upper and lower endplate facing surfaces 470, 480 and forms a substantially rectangular shape surrounding two hollow cores 420, 430. The hollow cores 420, 430 are disposed laterally to each other and are separated by internal walls 450 and a central graft compartment 460. The hollow cores 420, 430 and the graft compartment 450 extends from the upper endplate facing surface 470 to the lower endplate facing surface 480. Separate injection ports 440 in the sidewall 410 provide for the independent control of injection pressure, the amount of cement, and/or the type of cement that is injected into each of the hollow cores 420, 430 and that contacts each of the vertebral surfaces, respectively, which are directly above and below the device. In further embodiments, the upper endplate and lower endplate facing surfaces 470, 480 can include teeth structures (such as those illustrated in FIG. 1) to resist dislocation within and/or expulsion from the intervertebral space.

Figure 10:
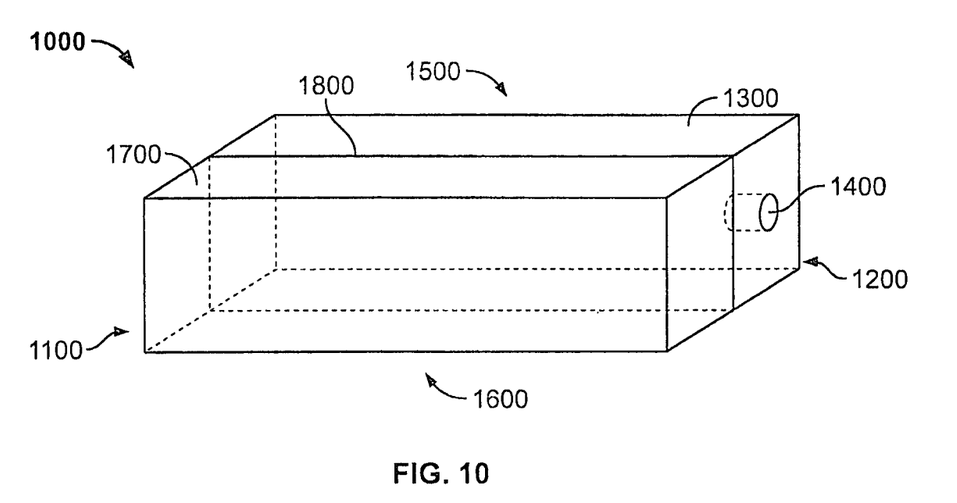
FIG. 10 is a perspective view of a fusion device of the invention configured for insertion by posterior surgical approach.
Figure 11:
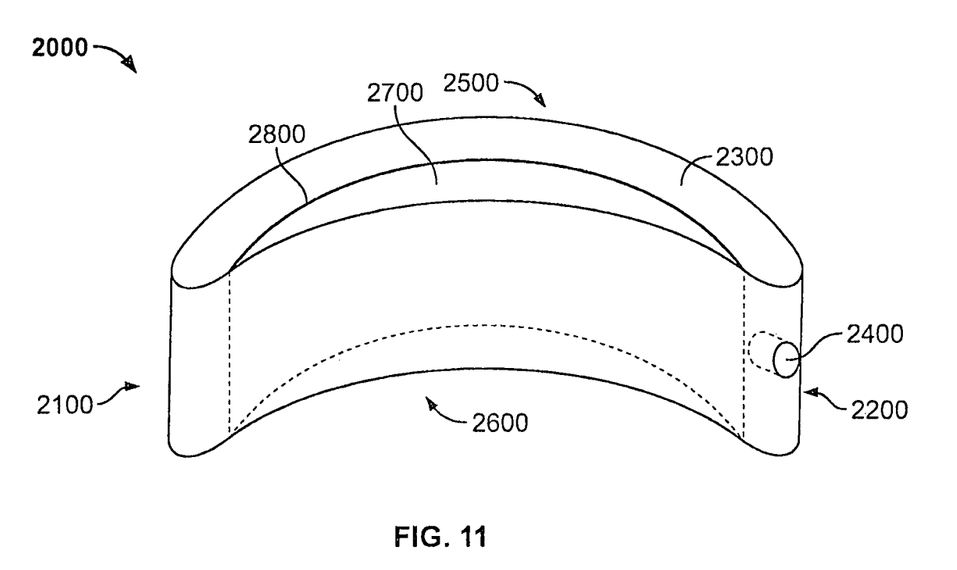
FIG. 11 is a perspective view of a fusion device of the invention configured for insertion by posterior surgical approach.

The spinal fusion device of the invention can be configured for insertion into the intervertebral space between adjacent upper and lower vertebra using a posterior or posterior lateral surgical approach. FIGS. 10 and 11, for example, illustrate devices of the invention suitable for insertion by a posterior or posterior lateral approach.

FIG. 10 illustrates a spinal fusion device 1000 with an outer surface 1100, 1200, 1500, 1600 having a substantially narrow rectangular shape. Using a posterior surgical incision, the insertion end 1100 of the device 1000 can be guided into the intervertebral space prior to positioning the trailing end 1200 in the intervertebral space, thereby allowing the fill port 1400 on the trailing end 1200 to remain accessible via the same posterior surgical incision. A delivery device can be inserted into the same posterior surgical incision to deliver cement to fill port 1400 until the cement fills the hollow core 1300 and is directed through openings in the upper and lower endplate facing surfaces 1500, 1600 to contact the upper and lower vertebral surfaces that are directly above and below, respectively, the device 1000. An internal wall 1800 separates the graft compartment 1700, which is for receiving bone graft material, from the hollow core 1300. The graft compartment, preferably extends from the upper endplate facing surface 1500 to the lower endplate facing surface 1600. In further embodiments, the upper endplate and lower endplate facing surfaces 1500, 1600 can also include teeth structures (such as those illustrated in FIG. 1) to resist dislocation within and/or expulsion from the intervertebral space.

FIG. 11 illustrates a spinal fusion device 2000 with an outer surface 2100, 2200, 2500, 2600 having a substantially boomerang shape. Using a posterior surgical incision, the insertion end 2100 of the device 2000 can be guided into the intervertebral space prior to positioning the trailing end 2200 in the intervertebral space, thereby allowing the fill port 2400 on the trailing end 2200 to remain accessible via the same posterior surgical incision. A delivery device can be inserted into the same posterior surgical incision to deliver cement to fill port fill port 2400 until cement fills the hollow core 2300 and is directed through openings in the upper and lower endplate facing surfaces 2500, 2600 to contact the upper and lower vertebral surfaces that are directly above and below, respectively, the device 2000. An internal wall 2800 separates the graft compartment 2700, which is for receiving bone graft material, from the hollow core 2300. The graft compartment, preferably extends from the upper endplate facing surface 2500 to the lower endplate facing surface 2600. In further embodiments, the upper endplate and lower endplate facing surfaces 2500, 2600 can also include teeth structures (such as those illustrated in FIG. 1) to resist dislocation within and/or expulsion from the intervertebral space.

In particular embodiments, the spinal fusion device of the invention includes and insertion end that is smaller than the trailing end. This configuration facilitates insertion of the device, and it may also be used to maintain, improve, or restore the appropriate curvature of the spine. Thus, the configuration of the devices illustrated in FIGS. 1, 2, 3, 4, 10, and 11 can be modified, for example, by tapering or otherwise altering their sidewall surface, to include smaller insertion end relative to the trailing end.

The spinal fusion device of the invention can also be configured to maintain, improve, or restore the appropriate lordotic angle in a patient's lumbar spinal region. In these configurations, the spinal fusion device's sidewall includes a taller portion to be positioned anteriorly in the lumbar intervertebral space and a shorter portion to be positioned posteriorly in the intervertebral space. In this context, taller and shorter refer to relative height, where height refers to the smallest distance between the lower endplate facing surface and the upper endplate facing surface at the anterior and posterior portions of the sidewall. Thus, the devices illustrated in FIGS. 1, 2, 3, 4, 10, and 11 can be modified, for example, by tapering or otherwise altering their sidewall surface, to include a taller anterior height and a shorter posterior height. In particular, the height of the anterior portion of the device can range from about 12 mm to about 20 mm. The height of the posterior portion the device is such that the device is said to provide a lordotic angle ranging from about 4 degrees to about 12 degrees. The lordotic angle of the device refers generally to the angle of the upper and lower endplate facing surfaces with respect to the other. The lordotic angle can also be calculated by drawing two lines that connect the points used to determine the anterior and posterior heights; Specifically, a first line is drawn that connects the two points used to determine height along the anterior and posterior portions of the upper endplate facing surface (these two points are disposed on the edge joining the upper endplate surface to the anterior sidewall or to the posterior sidewall portion used to determine anterior and posterior height, respectively), a second line is line is drawn that connects the two points used to determine height along the anterior and posterior portions of the lower endplate facing surface (these two points are disposed on the edge joining the lower endplate surface to the anterior sidewall or to the posterior sidewall portion used to determine anterior and posterior height, respectively), and the angle at which these two lines intersect is said to be the lordotic angle provided by the device.

The spinal fusion device of the invention may also includes structures that facilitate gripping and manipulating the device, e.g., by a clamp on the end of an inserter. For example, a rigid spinal fusion device may include one or more notches on opposite portions of the sidewall. The notches can receive the jaws of a clamp head, which can thereby tightly grip an manipulate the fusion device. In another example, the device can include one or more slits into which one or more flat heads at the end of an inserter can be inserted. The slits act as sleeves for the inserter and provide a stable grip for manipulating the device.

If desired, the spinal fusion device may include a plurality of outlets in the upper and lower endplate facing surfaces that are sized and positioned to allow cement material to flow from the hollow core and into contact with adjacent vertebral bone surfaces, which are directly above and below the device. The outlet size can be further selected to allow tissue ingrowth and should be from 100 microns to 3 mm in diameter, 250 microns to 2 mm in diameter and more preferably 500 microns to 1.5 mm in diameter.

In alternative embodiments of the invention, a delivery device, such as a syringe or other injection device as are known in the art, containing cement material is positioned with its tip inserted into the outlet (i.e., instead of a filler port) to inject cement into the hollow core. The outlet or plurality of outlets allows cement to exit the hollow core as it is filled with cement. The exiting cement contacts the adjacent vertebral endplate and polymerizes to fuse the spinal fusion device to the endplate.

In embodiments of the spinal fusion device of the invention that include one or more internal walls that separate one or more hollow cores and/or graft compartments and can contact the upper and/or lower vertebral surfaces when inserted in a vertebral space, such internal walls can include a roughened surface or surface porosity to mechanically interlock the cement to the device. Thus, for example, internal walls 250 in FIG. 2, 360 in FIG. 3, 450 in FIG. 4, 1800 in FIG. 10 and 2800 in FIG. 11 can be fashioned to include a roughened surface or surface porosity at their surfaces that contact the upper and/or lower vertebral surfaces.

The cement material can be injected into the spinal fusion implant device before and/or preferably after insertion of the implant into the intervertebral space. The implants of the invention can be inserted into the intervertebral space using conventional techniques and known tools, as well as using tools to distract the vertebrae to facilitate insertion of the implant into the intervertebral space. When the cement is injected into the implant prior to insertion of the implant into the intervertebral space, it is important that the implant be inserted prior to substantial polymerization (i.e., hardening) of the cement, preferably within about 2 minutes to within about 30 minutes of mixing the cement components.

In a separate aspect, the invention also provides a flexible spinal fusion device with an outer surface that is made of a biocompatible flexible material. Suitable biocompatible flexible materials for the outer surface include polymer fibers such as polyethylene, Teflon®, polyesters, Lycra®, nylon, rayon, cellulose, and the like. Other suitable flexible materials can be composed of resorbable fibers or sheets, such as polylactic acid, polyglycolic acid, polylactic/polyglycolic acid copolymers, polypropylenefumarate, polypropyleneitaconate, polyhydroxybutyric acid, polyhydroxyvaleric acid, polycaprolactone, polyhydroxycarboxylic acids, polybutyrene succinate, polybutylene adipate, polytyrosine carbonates, polytyrosine carbonates, polydioxanes, collagen, chitosan, alginate, cellulose, starches, sugars, polypeptides, polyethylene glycol, vinyl pyrrolidones, acrylamides and methacrylates or any of their derivates, poly(valerolactone), poly(trimethylene carbonate), poly(imino carbonates), poly(tartonic acid), poly(13-malonic acid), aliphatic disisocyanate based polyurethanes, peptide-based polyurethanes, polyester or polyorthoester based polyurethanes, polyphosphazenes incorporating amino acid ester, glucosyl, glyceyl, lactate or imidazolyl side groups, and combinations thereof.

Referring now to FIGS. 5 to 8, flexible fusion devices 500, 600, 700, 800 in accordance with a separate aspect of the invention are depicted. Generally, the flexible fusion device of the invention is compactable prior to filling with cement and/or bone graft material and expandable when filled with cement. In its compacted form, the flexible fusion device is suitable for delivery via minimally invasive procedures to the intervertebral space between two adjacent vertebra. Preferably, only portions of the flexible implant facing the vertebral endplates are permeable to cement. More specifically, it is preferable that at least one of the endplate facing surfaces is permeable to cement and that the sidewall or sidewalls are impermeable to cement. More preferably, the endplate facing surface is permeable due to the presence of a plurality of pores that are of sufficient diameter so as to allow passage of cement. In this regard, the pores can generally be from about 10 microns to about 5 mm in diameter.

Advantageously, the flexible spinal fusion device of the invention can be inflated by injecting cement into one or more hollow cores to restore disc height. The devices can further include a graft compartment for receiving bone graft materials, which, as used herein, can include biological additives, such as orthobiologicals, including allografts, autografts, demineralized bone matrix, collagen, growth factors, or bone morphogenic proteins. The hollow core and/or graft compartments are preferably configured so that cement provides structural support across the entire length and width of the implant.

Figure 5:
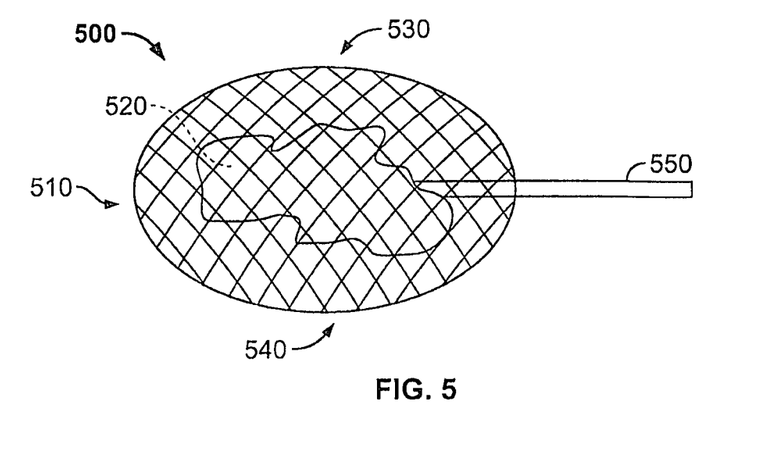
FIG. 5 is a perspective view of a cannula and a flexible fusion device of the invention with a flexible outer surface.

FIG. 5 illustrates a flexible spinal fusion device 500 that includes an outer surface 510, 530, 540 made of flexible material, in accordance with another embodiment of the invention. The sidewall 510 is formed between an upper endplate facing surface 530 and a lower endplate facing surface 540. The outer surface 510, 530, 540 can be pierced by a cannula 550 for injecting cement into the hollow core 520, which is surrounded by the outer surface 510, 530, 540. In preferred embodiments, the outer surface 510, 530, 540 is made of a sheet and a woven or mesh material that allows for varying degrees of permeability by the injected cement. For a cement having a particular viscosity, permeability can be controlled by weave or mesh density. Thus, the upper and lower endplate facing surfaces 530, 540 can be made of a relatively loose weave or mesh that allows injected cement to permeate from the hollow cavity 520 and contact the upper and lower endplate facing surfaces, respectively. The longitudinal outer surface 510 is preferably made from a denser weave or finer mesh that is impermeable to the cement, thereby restricting and directing the flow of cement towards the inferior and or inferior vertebral bodies. In this regard, it is further noted that cement permeability is a function of both (i) the quality (density or fineness) of a weave or mesh in the flexible material and (ii) the viscosity of the cement used. The flexible device 500 expands upon filling with cement, and eventually releases cement onto vertebral surfaces in contact with pores or openings in the vertebral facing surfaces 530, 540 of the implant. Advantageously, the flexible implant can be filled to desired levels to occupy a predetermined volume and provide an implant of desired height and structural support.

Figure 6:
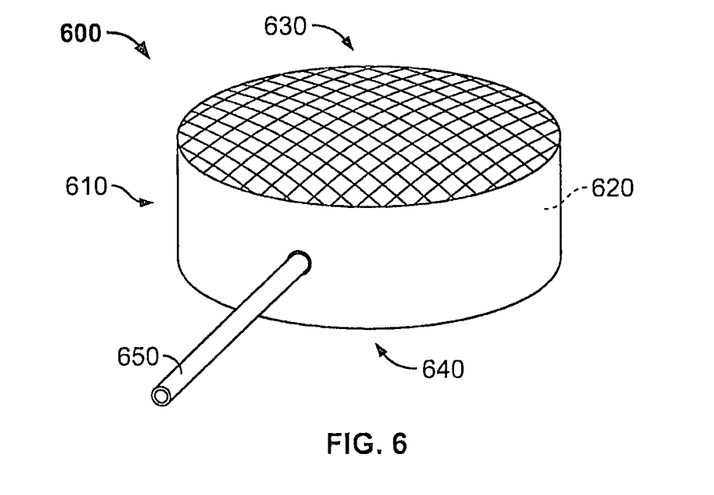
FIG. 6 is a perspective view of a cannula and a flexible fusion device of the invention with a flexible outer surface that includes an impervious side wall and mesh top.

FIG. 6 illustrates another flexible spinal fusion device 600 according to the invention having an outer surface 610, 630, 640 made of flexible material. In this embodiment, the upper endplate facing surface 630, the lower endplate facing surface 640, and the sidewall 610 therebetween form a substantially disc shaped device 600. The sidewall 610 can be pierced by a cannula 650 to inject cement into the hollow cavity 620, which is surrounded by the outer surface 610, 630, 640. Preferably sidewall 610 is made of material that is solid (yet flexible), that includes a cement barrier sheet, or that includes a sufficiently fine mesh or dense weave so as to make the sidewall 610 substantially impermeable to cement injected into the hollow core 620. The upper and lower endplate facing surfaces 630, 640 are made of a sufficiently open mesh or loose weave, which allows injected cement to permeate from the hollow core 620 towards the upper and lower endplates, respectively, of adjacent vertebral bodies.

Figure 7:
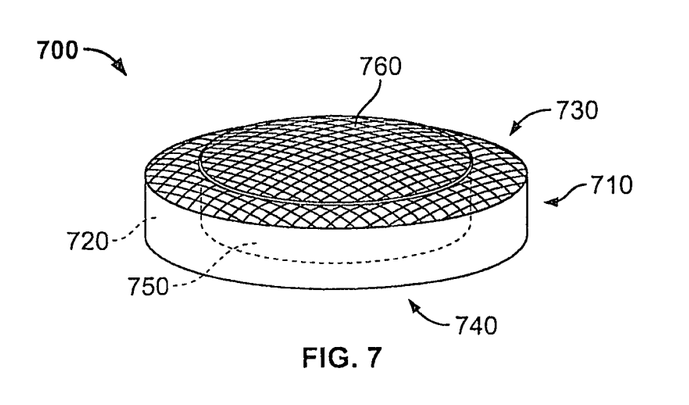
FIG. 7 is a perspective view of a flexible fusion device of the invention with a flexible outer surface and a graft compartment.

FIG. 7 illustrates yet another flexible spinal fusion device 700 according to the invention having an outer surface 710, 730, 740 made of flexible material. Cement can be injected into the hollow core 720. The device 700 also includes a central graft compartment 760 for bone graft material, which is separated from the hollow core 720 by an inner wall 750. The inner wall 750 is preferably a woven mesh barrier that is impermeable to cement injected into the hollow core 720, yet permeable to body fluids. Alternatively, the inner wall 750 can be made of a sheet that is impermeable to both cement and body fluids. The upper and lower endplate facing surfaces 730, 740 are made of an open mesh that (a) allows injected cement to permeate from the hollow core 720 through the upper and lower endplate facing surfaces 730, 740, respectively, and towards upper lower adjacent vertebrae, respectively and (b) also permits the ingrowth of bone tissue from the vertebral body into the graft compartment 760. In this regard, in some embodiments, it may be desirable to vary the density of the mesh or weave of the upper and lower endplate facing surfaces 730, 740 as between the portions that surround the hollow core 720 and the portions that surround the graft compartment 760.

Figure 8:
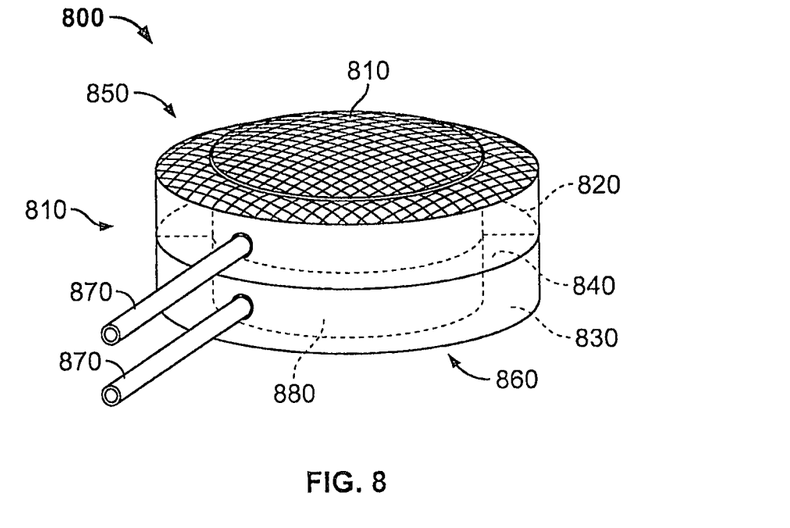
FIG. 8 is a perspective view of a flexible fusion device of the invention with a flexible outer surface that includes separate upper and lower hollow cores for cement as well as a graft compartment.

FIG. 8 illustrates another flexible spinal fusion device 800 according to the invention having an outer surface 810, 850, 860 made of flexible material and that includes an upper hollow core 820 and a lower hollow core 830, which are separated from each other by a midsection wall 840. The device 800 also includes a central graft compartment 810 for bone graft material, which is separated from both hollow cores 820, 830 by an interior wall 880. Cement can be injected independently into each of the upper and lower cores 820, 830 by way of separate cannulas 870 or separate insertions of the same cannula. When the upper and lower hollow cores 820, 830 are separated by a cement impermeable a midsection wall 840, the flexible fusion device 800 provides for the independent control of injection pressure, amount of injected cement, and types of injected cement for each hollow core. The upper and lower endplate facing surface 850, 860 are made of an open mesh that (a) allows injected cement to permeate from each of upper and lower hollow cores 820, 830 through the upper and lower endplate facing surfaces 850, 860, respectively, and towards upper lower adjacent vertebrae, respectively and (b) also permits the ingrowth of bone tissue from the vertebral body into the graft compartment 810. In this regard, in some embodiments, it may be desirable to vary the density of the mesh or weave of the upper and lower endplate facing surfaces 850, 860 as between the portions that surround the hollow cores 820, 830 and the portions that surround the graft compartment 810.

In other embodiments of the invention, a flexible spinal fusion device can further include one or more fill ports in the outer surface for injecting cement into the one or more hollow cores of the flexible device. In these embodiments, these flexible device does not require piercing the outer surface to inject cement.

The flexible spinal fusion device is advantageous because it specifically contemplates and allows for a minimally invasive procedure for insertion into the intervertebral space. In this regard, the flexible implant is capable of being compacted to fit within a cannula and inserted through a cannula-sized incision and into the intervertebral space, which can be repaired once the flexible device is implanted. Upon positioning, the flexible implant can be filled with cement so that the implant expands to the desired volume in the intervertebral space. Cement material may be further injected into the flexible implant so that the cement permeates through the endplate facing surfaces of the device and contacts one or more of the adjacent vertebral endplates to facilitate fusion of the vertebrae as the cement sets.

Generally, when a spinal fusion device of the invention includes multiple hollow cores, each cavity can be independently filled with the appropriate amount of cement needed to achieve mechanical stabilization of the vertebral motion segment. The use of separate injection ports in a device of the invention can also promote the maintenance of uniform injection pressure (for example in the superior and inferior hollow cavity), which, thereby, produces a more uniform cement fill in the space between vertebral bodies.

The rigid spinal fusion devices of the invention can be formed of any suitable load bearing, biocompatible material. Suitable materials include bioceramic materials, stainless steel, cobalt chrome, titanium alloy such as Ti6Al4V alloys, polymers such as PEEK, resorbable polymers, resorbable polymer composites, bone grafts, and the like.

Preferred bioceramics can be made by the methods described in RE 39,196 and U.S. application Ser. No. 10/635, 402, which are hereby incorporated by reference herein in their entirety.

The implants of the invention desirably have a resorption time of about 1 month or more (e.g., about 3 months or more, about 6 months or more, or about 1 year or more). The rate of resorption will depend at least in part on the crystal size and the composition of the implant. Smaller crystal sizes will be resorbed more rapidly than larger crystal sizes. The desired resorption rate will depend on the application and the crystal size and composition can be tailored to match a desired resorption rate. In some applications, it is desired that the resorption time be about 6 months or more (e.g., about 1 year or more, or about 2 years or more).

The cements useful in the invention include biocompatible, injectable cements that set in vivo with sufficient strength to provide mechanical stabilization of adjacent vertebrae. Properties of suitable cements can include one or more of the following:

1. A low exotherm, for example, an exotherm of less than 50° C.

2. Radiopacity

3. The ability to be injected through a narrow gauge needle or cannula such as those no larger than 1 gauge, 3 gauge, 5 gauge, 7 gauge, 8 gauge, 9 gauge, 10 gauge, 11 gauge, 12 gauge, 13 gauge, 14 gauge, or 15 gauge. Preferably, the cements are injectable through a narrow gauge needle or cannula less than about 1 gauge, more preferably less than about 3 gauge, 5 gauge, 7 gauge, 8 gauge, 9 gauge, 10 gauge, 11 gauge, 12 gauge, 13 gauge, 14 gauge, or 15 gauge.

4. Set times of less than 30 minutes, less than 25 minutes, less than 20 minutes, less than 15 minutes, less than 10 minutes, less than 5 minutes in vivo. Set time refers to the time it takes for a cement to first develop compressive strength. Compressive strength can be measured using compression testers or other suitable devices. Protocols for measuring set time and compression strength are known in the art and are described in, for example, ASTM F451 (Standard Specification for Acrylic Bone Cement), ASTM D695 (Test method for compressive properties of rigid plastics), and ASTM C773 (Standard Test Method for Compressive (Crushing) Strength of Fired Whiteware Materials). ASTM tests are published by ASTM International (West Conshohocken, Pa.).

5. A strength after setting for 1 hour of 10% of final cure strength in terms of compression, 20% of final cure strength, 30% of final cure strength, 40% of final cure strength, 50% of final cure strength, 60% of final cure strength, 70% of final cure strength, 80% of final cure strength, 90% of final cure strength and 100% of final cure strength.

6. A strength after setting for 6 hour of 10% of final cure strength in terms of compression, 20% of final cure strength, 30% of final cure strength, 40% of final cure strength, 50% of final cure strength, 60% of final cure strength, 70% of final cure strength, 80% of final cure strength, 90% of final cure strength and 100% of final cure strength.

7. Cure time, defined as time needed to achieve maximum compressive strength, of from about 5 minutes to 24 hours (e.g. about 5 minutes to 20 hours, about 5 minutes to 12 hours, about 5 minutes to 6 hours, about 5 minutes to 3 hours, about 5 minutes to 1.5 hours, about 5 minutes to 45 minutes).

8. a minimum compressive strength after curing of at least about 10 MPa, more preferably at least about 20 MPa, 30 MPa, 40 MPa, 50 MPa, 60 MPa, 70 MPa, 80 MPa, 90 MPa, 100 MPa, 125 MPa, 150 MPa, 175 MPa, 200 MPa, 250 MPa, or 300 MPa.

9. strength maintenance of at least about 5 percent to 100 percent of its initial strength (e.g. about 5 percent to 75 percent, about 5 percent to 50 percent, about 5 percent to 30 percent, about 5 percent to 15 percent) for at least about 24 months (e.g. about 18 months, about 12 months, about 6 months).

10. a pH of about 4 to about 8.5 (e.g. about 4 to about 8, about 5 to about 8) when aged in body fluids, simulated body fluids, DI water, TRIS Buffer, Saline Buffer, Ringer's Lactate, Phosphate Buffer Solution having a pH from about 4 to about 8.5 on the cement after submergence in the fluid for a minimum about 2 days (e.g. 4 days, about 1 week, about 1 month, about 1 year).

11. biocompatibility according to ISO 10993—"Biological Evaluation of Medical Devices."

Clinically used cements that can be used in conjunction with the devices of the invention include, for example, those based on the polymerizable acrylate resin polymethylmethacrylate (PMMA) and calcium phosphate cements. While either of these cements can be used with the devices of the invention, they are not always desirable. Although, PMMA may be strong enough for use in conjunction with the device in standalone application, its high exotherm and lack of osteoconductivity, osteoinductivity and resorbability make it undesirable for clinical applications where boney ingrowth and replacement are desirable clinical sequalae. Alternatively, calcium phosphate cements are osteoconductive and resorbable and be used to deliver osteoinductive agents, but they do not possess the strength for a standalone fusion applications, and thus may require the use of adjuvant fixation devices.

Preferred cements include (1) polymer reinforced calcium phosphate cements; (2) composite cements such as PMMA cements comprising a filler such as glass, bone, or calcium phosphate; (3) composite cements containing (i) poly(meth)acrylate resins and (ii) a filler such as glass, bone, or calcium phosphate; (4) composite cements containing (i) isocyanate resins that are polymerized to polyurethanes or polyurea and (ii) a filler such as glass, bone, or calcium phosphate; (4) glass ionomer cements, and the like. One or more of the cement components can also, optionally, include additional materials, such as inert fillers or bioactive components that promote bone growth. These cements either improve upon the mechanical properties of calcium phosphate cements or upon the osteoconductivity and bone bonding ability of poly(metha)acrylate or isocyanate resins.

The most preferred embodiments for the cement in standalone applications are cements that are mechanically robust and would allow for bone bonding, boney ingrowth and boney replacement. In preferred embodiments, the cement comprises an injectable cement described in U.S. patent application Ser. No. 11/500,798, which published as US 20070032568 A1, and/or U.S. Provisional Application No. 60/968,462, filed on Aug. 8, 2007, the entire contents of both of which are specifically incorporated by reference herein. The cements described in these applications, generally include a first component and a second component. The first component comprises a polymerizable resin with an ethylenic unsaturated double bond. Alternatively, in addition to or instead of the ethylenic unsaturated double bond, the first component comprises a polymerizable resin that includes a suitable glycidyl ether; a suitable glycidyl ester; a suitable ester containing glycidyl ether; a suitable carbonate containing glycidyl ether; a suitable ester or carbonate containing isocyanate. Thus, the first component can also comprise of a mixture of ethylenic unsaturated double bonds, glycidyl groups or isocyanate groups. The second component includes a compound that includes more than one type of amine selected from the group consisting of a primary amine, a secondary amine, a tertiary amine, or a quaternary amine. Alternatively, the second component includes a compound comprising a suitable mercapto (—SH) group or acetoacetonate group. The compounds in the second component can be further functionalized with ester or carbonate groups. Among those described in U.S. patent application Ser. No. 11/500, 798, which published as US 20070032568 A1, and/or U.S. Provisional Application No. 60/968,462, the entire contents of both of which are specifically incorporated by reference herein, ore preferred cements include a first component that comprises at least one ethylenic unsaturated double bond and an epoxide, such as a glycidyl group, and, optionally, at least one ester or carbonate group. In these preferred cements, the second component includes a polyalkyleneimine, such as polyethyleneimine (PEI) or a derivative thereof, and, optionally the second component comprises a mixture of a polyalkyleneimine or a derivative thereof and a polyalkylamines, polyesteramines, fatty acid amines, lipopolyamines or derivatives thereof.

Polymerizable resins suitable for the first component include acrylic resins. Suitable acrylic resins include methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate ("HEMA"), hydroxypropyl acrylate, hydroxypropyl methacrylate, tetrahydrofurfuryl acrylate, tetrahydrofurfuryl methacrylate, glycerol mono- and di-acrylate, glycerol mono- and dimethacrylate, ethyleneglycol diacrylate, ethyleneglycol dimethacrylate, polyethyleneglycol diacrylate where the number of repeating ethylene oxide units vary from 2 to 30, polyethyleneglycol dimethacrylate where the number of repeating ethylene oxide units vary from 2 to 30, especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexamethylene dicarbamate, di-2-methacryloyl oxyethyl dimethylbenzene dicarbamate, methylene-bis-2-methacryloxyethyl-4-cyclohexyl carbamate, di-2-methacryloxyethyldimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethylhexamethylene dicarbamate, di-1-chloromethyl-2-methacryloxyethyltrimethylhexamethylenedicarbamate, di-1-chloromethyl-2-methacryloxyethyldimethylbenzenedicarbamate, di-1-chloromethyl-2-methacryloxyethyldimethylcyclohexanedicarbamate, methylene-bis-2-methacryloxyethyl-4-cyclohexylcarbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-ethacryloxyethyldimethylcyclohexanedicarbamate, methylene-bis-1-methyl-2-methacryloxyethyl-4-cyclohexyl carbamate, di-1-chloromethyl-2-methacryloxyethyl-hexamethylenedicarbamate, di-1-chloromethyl-2-methacryloxyethyl-trimethylhexamethylenedicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'-bis(4-acryloxyphenyl)propane, 2,2'-bis[4(2-hydroxy-3-methacryloxy-phenyl)]propane, 2,2'-bis 4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)

propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acrylate]propane, propoxylated (2) neopentylglycol diacrylate (Sartomer SR9003), isobornyl methacrylate (Sartomer SR423), aromatic acrylate oligomer (Sartomer CN137), aliphatic allyl oligomer (Sartomer CN9101), dimethylaminoethyl methacrylate (DMAEMA), methylene bisacrylamide (MBA), dimethylaminopropylmethacrylamide, methacrylamidopropyltrimethylammonium chloride and the like. All products designated herein by reference to "Sartomer" and product number are available from Sartomer Company, Inc. (Exton, Pa.).

Other suitable examples of polymerizable resins can include polymerizable groups selected from isopropenyl oxazoline, vinyl azalactone, vinyl pyrrolidone, styrene, divinylbenzene, urethane acrylates, urethane methacrylates, polyol acrylates, and polyol methacrylates. In certain embodiments, the first component can include polylactic acid (D and L), polyglycolic acid, polylactic/polyglycolic acid copolymers, vinyl group containing polyesters such as polypropylenefumarate and polypropyleneitaconate, polydioxane, poly(e-caprolactone), poly(valerolactone), poly(trimethylene carbonate), poly(tyrosine-carbonates) and poly(tyrosine-arylates), poly(imino carbonates), poly(hydroxybutyrate) (PHB), poly(hydroxyvalerate), poly(tartonic acid), poly(b-malonic acid), polyhydroxycarboxylic acids, polybutyrene succinate, polybutylene adipate, aliphatic disisocyanate based polyurethanes, peptide-based polyurethanes, polyester or polyorthoester based polyurethanes, polyphosphazenes incorporating amino acid ester, glucosyl, glyceyl, lactate or imidazolyl side groups, collagen, chitosan, alginate, cellulose, starches, sugars, polypeptides, polyethylene glycol, vinyl pyrrolidones, acrylamides and methacrylates or any of their derivates or copolymers. In certain preferred embodiments, the first component comprises a resorbable material that is flowable at room temperature comprising polymerizable functional groups, such as vinyl group containing polyesters such as polypropylenefumarate and polypropyleneitaconate.

Accordingly, preferred polymerizable resins for the first component include ethoxylated trimethylolpropane triacrylate, epoxy acrylate, modified epoxy acrylate (e.g., Sartomer CN115), bisphenol A epoxy methacrylate oligomer (Sartomer CN-151), aliphatic acrylate modifier (Sartomer MCURE 201 and Sartomer MCURE400), glycidyl acrylate of bis-phenol A and the diglycidyl methacrylate of bis-phenol A (bis-GMA). Useful epoxy-containing materials also include those which contain cyclohexene oxide groups such as the epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature; see U.S. Pat. No. 3,117,099, incorporated herein by reference.

Additionally, preferred polymerizable resins of the first component include (i) glycidyl esters of neodecanoic acid (ERISYS GS-110), of Linoleic Acid dimmer (ERISYS GS-120), both from CVC Specialty Chemicals (Moorestown, N.J.), other glycidyl ester such as diglycidyl separate, diglycidyl azelate, diglycidyl pimelate, diglycidyl adipate, diglycidyl succinate, diglycidyl oxalate, and olyglycidyl(meth)acrylate, and the like, (ii) glycidyl ethers such as poly[(phenyl glycidyl ether)co-formaldehyde], N,N-diglycidyl-4-glycidyloxyaniline ether, neopentyl glycol diglycidyl ether; Bisphenol A propoxylate (1 PO/phenol) diglycidyl ether, ARALDITE GY 281 (Bisphenol F epoxy resin with moderate viscosity), ARALDITE 506 (Bisphenol A epoxy resin), (ARALDITE products are from Huntsman, Woodlands, Tex.), castor oil triglycidyl ether (ERISYS GE-35), sorbitol polyglycidylether (ERISYS GE-60), trimethylpropane triglycidyl ether (ERISYS GE-30), 1,6-hexanediol diglycidyl ether (ERISYS GE-25), cyclohexanedimethanol diglycidyl ether (ERERISYS GE-22), 1,4-butanediol diglycidyl ether (ERISYS GE-21), (all ERISYS resins are supplied from CVC Specialty Chemicals (Moorestown, N.J.), trimethylolethane triglycidyl ether, (1,4-butanediol diglycidyl ether), dibromo neopentyl glycol diglycidyl ether, neopentyl glycol diglycidyl ether, ethyleneglycol doglycidyl ether, polyglycidyl methacrylate, polyglycidyl acrylate, polyglycidylmethacrylate, polyglycidylacrylate, and the like, (iii) ester containing glycidyl ether groups such as CYRACURE UVR 6105 (3,4-epoxycyclohexylmethyl-3,4-epoxycyclohexane) from Dow-Union Carbide Corp (Danbury, Conn.), and the like, (iv) carbonate containing glycidyl ether groups such as DECHETOSU (oxirane-spiroorthocarbonate) from Midwest Research Institute (Kansas City, Mo.).

The second component of the cement product includes a compound comprising more than one type of amine selected from the group consisting of a primary amine, a secondary amine, a tertiary amine, and a quaternary amine. Suitable compounds for the second component include aliphatic polyamines, aromatic polyamines, or mixtures thereof. Polyamines that can be used in the second component include phenylenediamine, ethylenediamine, triethylenetetramine, and a wide variety of other aliphatic and aromatic diamines that polymerize when mixed with the polymerizable resin of the first component. Suitable compounds for the second component include modified polyamino acids such as polylysines and imidazole-modified polylysines. Suitable polyamines can include branched dendrimers with multiple types of amines, such as polyamidoamine (PAMAM) dendrimers.

Additional amine-containing compounds suitable for inclusion in the second component include monomers or oligomers further comprising ester, ether, amide, carbonate, urethane, or oxirane functional groups on the side chain or main chain. Preferred groups on the side chain or main chain include imide, imidine and isocyanate groups. Suitable amine-containing compounds of the of the second component can include, for example, oleylamine, stearylamine, 2-ethylhexylamine, ethylenediamine, propylenediamine, 1,6-hexamethylenediamine, aminoethanolamine, ethanolamine, propylenetriamine, butylenetriamine, diethylenetriamine, triethylenetetramine, tetraethylenepentamine, pentaethylenehexamine, menthanediamine, isophoronediamine, xylenediamine, tetrachloro-p-xylenediamine, methylenedianiline, diaminodiphenylsulfone, polyaniline, N-methylpiperazine, hydroxyethylpiperazine, piperidine, pyrrolidine, morpholine, diethanolamine, streptidine, stilbamidine, 2-deoxystreptamine, dapsone, p-diaminoazobenzene, 4,4'-diaminodiphenyl ether, and the like. Preferred suitable amine-containing compounds of the of the second component can include 1,4-diaminobutane, o-cyclohexanediamine, and m-phenylenediamine.

Still other amine-containing compound suitable for use in the second component include biological amines such as guanidine, uracil, thymine, adenine, guanine, cytosine, xanthine and their respective biological nucleotides or derivatives thereof. Exemplary derivative nucleotides include 2,4-diamino-6-hydroxy-pyrimidine and 2,6-diaminopurine. The second component can include oligomers, polymers and copolymers of amino acids such as arginine, tyrosine, cysteine, or lysine.

In addition to the compounds described herein, the second component can further include free amino acids, such as, arginine, tyrosine, cysteine, or lysine. These can enhance the curative hardening reaction of the second component with the first component.

Preferred amine-containing compounds of the second component include polyalkyleneamines and derivatives thereof such as polyethyleneimine (PEI) and PEI derivatives, polypropyleneimine (PPI) and PPI derivatives, which typically include primary, secondary and tertiary amines. The PEI or PEI derivative can also include quaternary amines. PEI derivatives include ethoxylated PEI, hydroxyethoxylated PEI, and hydroxypropylated PEI. The PEI or PEI derivatives can be branched or linear. Preferably the PEI or the PEI derivative has a sufficiently low molecular weight that it is a liquid. For example, the PEI or PEI derivative can have an average molecular weight of less than 200 kDa, less than 150 kDA, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 10 kDa, less than 5 kDa or less than 2 kDa. The PEI or PEI derivative can have an average molecular of less than about 2 kDa and more than about 0.2 kDa. Preferably, the PEI or PEI derivative has an average molecular weight of less than 1 kDa and greater than 0.3 kDa.

In preferred embodiments, the cement is also osteoconductive, osteoinductive and/or resorbable. Thus, as honey spinal fusion occurs, the cement can resorb and can act as scaffold that promotes tissue ingrowth without needing bone graft material, such as autograft material. Such cements can, however, also be used in conjunction with the spinal fusion device embodiments described herein, which include bone graft material in the one or more graft compartments. The chemistry of a suitable cement can be such that load bearing gradually shifts from the cemented vertebral construct to the bone growing in the disc space in preferred embodiments via the cement's inherent osteoconductivity, osteoinductivity and/or resorbability.

Osteoconduction refers to the ability of a materials to serve as a scaffold on which bone cells can attach, migrate (meaning move or "crawl"), and grow and divide. Osteoconductive materials need to be adjacent to bone to "conduct" bone cells. In this way, the bone healing response is "conducted" through the graft site, in a manner that is generally reminiscent of electricity being conducted through a wire. Osteogenic cells generally work much better when they have a matrix or scaffold to attach to. Osteoinduction implies the recruitment of immature cells and the stimulation of these cells to develop into preosteoblasts and into mature, forming healthy bone tissue. Most, but not all of these signals are protein molecules called, as a group, "peptide growth factors" or "cytokines." Common osteoinductive proteins include Bone Morphogenetic Proteins (BMPs), Epidermal Growth Factor (EGF), Platelet Derived Growth Factor (PDGF), Fibroblast Growth Factors (FGFs), Parathyroid Hormone Related Peptide (PTHrp), Insulin-like Growth Factors (IGFs), and Transforming Growth Factor-Beta (TGF-B).

The combination of osteoconductivity, osteoinductivty and resorbability will manifest itself as boney apposition, ingrowth and replacement of the cement in vivo. By 6 months in vivo, the boney apposition to the cement directly adjacent to bone will be least 10% surface coverage, 20%, 30%, 40%, 50%, 60%, 70%, or 80%. By 18 months in vivo, at least 5%, 10%, 20%, 30%, 40% or 50% volume of cement previously occupied by the cement will have been replaced with bone. By 36 months in vivo, at least 10%, 25%, 50% or 75% volume of cement previously occupied by the cement will have been replaced with bone.

In these cases, the chemistry of the cement is such that it can have osteoinductive and osteoconductive properties to facilitate honey ingrowth via tissue engineering methods. The cement can act as a scaffold by incorporating porosity into the cement via effervescing agent, such as sodium bicarbonate, or a more rapidly dissolving phase, such as sodium chloride salts, polyester microspheres. A more detailed description of methods for incorporating porosity is described in U.S. patent application Ser. No. 11/500,798, which published as US 20070032568 A1, and/or U.S. provisional application No. 60/968,462, filed on Aug. 8, 2007, the entire contents of both of which are specifically incorporated by reference herein. The porous cement should be mechanically robust enough to maintain the disc height as bone ingrowth occurs.

Whether or not it has porosity, the fully cured cement has a minimum compressive strength of about 10 MPa, 20 MPa, 30 MPa, 40 MPa, 50 MPa, 60 MPa, 70 MPa, 80 MPa, 90 MPa, 100 MPa, 125 MPa, 150 MPa, 175 MPa, 200 MPa, 250 MPa, or 300 MPa or more; a minimum tensile strength of about 5 MPa, 10 MPa, 15 MPa, 20 MPa, 25 MPa, 30 MPa, 35 MPa, 40 MPa, 45 MPa, 50 MPa, 60 MPa, 70 MPa, 80 MPa, 100 MPa, 125 MPa, or 150 MPa or more; a minimum flexural strength of about 10 MPa, 15 MPa, 20 MPa, 25 MPa, 30 MPa, 35 MPa, 40 MPa, 45 MPa, 50 MPa, 60 MPa, 80 MPa, 1000 MPa, 125 MPa, 150 MPa, or 200 MPa or more; a minimum shear strength of about 10 MPa, 15 MPa, 20 MPa, 25 MPa, 30 MPa, 35 MPa, 40 MPa, 45 MPa, 50 MPa, 60 MPa, 80 MPa, 1000 MPa, 125 MPa, 150 MPa, or 200 MPa or more; and/or a minimum elastic modulus of about 300 MPa, 500 MPa, 700 MPa, 900 MPa, 1100 MPa, 1300 MPa, 1500 MPa, 1750 MPa, 2000 MPa, 2500 MPa, 3000 MPa, 3500 MPa, 4000 MPa, 5000 MPa, or 6000 MPa or more.

Desirable mechanical strength properties include the following. Compressive strength can be from about 20 MPa to about 250 MPa, typically from about 50 MPa to about 250 MPa, and preferably about 50 MPa or more, about 100 MPa or more, or about 150 MPa or more. A preferred tensile strength is from about 10 to about 100 MPa (e.g., about 20 MPa or more, about 40 MPa or more, or about 60 MPa or more). A preferred shear strength is from about 30 MPa to about 150 MPa (e.g., about 50 MPa or more, about 80 MPa or more, or about 110 MPa or more). A preferred flexural strength is from about 20 MPa to about 100 MPa (e.g., about 30 MPa or more, about 40 MPa or more, or about 50 MPa or more).

A preferred infinite compression fatigue is from about 20 MPa to about 150 MPa (e.g., about 40 MPa or more, about 70 MPa or more, or about 100 MPa or more). A preferred tensile fatigue is from about 5 MPa to about 40 MPa (e.g., about 10 MPa or more, about 20 MPa or more, or about 30 MPa or more).

The compression modulus typically is in the range of about 20 MPa to about 5 GPa, preferably in the range of about 50 MPa to about 2 GPa, and more preferably in range of about 100 MPa to about 1 GPa. The deformation percentage ranges from about 10 percent to about 90 percent, preferably from about 20 percent to about 80 percent and more preferably from about 30 percent to about 50 percent.

The different types of mechanical strengths can be measured according to tests known in the art, such as ASTM F451 (Standard Specification for Acrylic Bone Cement), ASTM D695 (Test method for compressive properties of rigid plastics), and ASTM C773 (Standard Test Method for Compressive (Crushing) Strength of Fired Whiteware Materials). ASTM tests are published by ASTM International (West Conshohocken, Pa.).

The invention further provides a spinal fusion system that includes (a) a spinal fusion device of the invention and (b) a suitable amount of cement or cement components that, when mixed, form a suitable amount of cement that is sufficient to fill the hollow cavity of the fusion device and to contact the upper vertebral body; the lower vertebral body; or both the upper and the lower vertebral bodies that contact the implanted spinal fusion device. Suitable amounts of cement are further described herein. The system can also include bone graft material. Optionally, the system can include one or more adjuvant fixation devices. The systems of the invention can be packaged for commercial distribution and sale. Preferred systems of the invention can include (a) a spinal fusion device of the invention with a body formed from a resorbable material described herein, such as the densified or consolidated hydroxyapatite or tricalcium phosphate, in particular the nanocrystalline material, described in U.S. Pat. No. 6,013,591, reissued as RE 39,196, and U.S. patent application Ser. No. 10/635,402, which published as U.S. 2005/0031704 A1, the entire contents of all three of which are specifically incorporated by reference herein, and (b) the preferred injectable cement embodiments as described herein and which are disclosed in U.S. patent application Ser. No. 11/500,798, which published as US 2007/0032568A1, and/or U.S. Provisional Application No. 60/968,462, filed on Aug. 8, 2007, the entire contents of both of which are specifically incorporated by reference herein.

The invention also provides spinal fusion methods that include inserting the fusion device of the invention between a superior and an inferior vertebral body of a subject in need of spinal fusion. The fusion device has any suitable shape to fit between adjacent vertebrae and has a sufficient height to maintain disc height between vertebrae. The implant may be shaped to fit a range of sizes of intervertebral spaces, such as ranging from cervical to lumbar intervertebral spaces. The endplate facing surfaces are preferably contoured to match the contour of the vertebral endplates so that the openings of the implant deliver cement to the vertebrae, not the intervertebral space surrounding the implant. To facilitate implantation, a surgeon may also cut or mill the vertebral endplate to provide a desired shape or contour. For example, if the surgeon prepares the endplates to be flat, it is preferred that the endplate facing surfaces are also flat. Likewise, if the endplates are prepared to be concave, it is preferred that the endplate facing surfaces are complementarily convex. It should be noted that endplates that are concave will generally retain the implant better since the device becomes cupped between the vertebrae.

Generally, the fusion device of the invention can be inserted between two vertebra using an anterior, a lateral, or a posterior surgical approach to access the cervical, thoracic and lumbar regions of the spine. If the access is anterior, the patient can be placed in a slight to hyper-flexion. If the access is posterior, the patient can be placed in a slight to hyper-extension. If the access is lateral, the patient can be placed in a slight to hyper-lateral flexion.

Spinal fusion surgery begins by accessing the disc space with a surgical incision that is preferably no more than about 30 cm in length, 25 cm in length, 20 cm in length, 15 cm in length, 10 cm in length, 8 cm in length, 6 cm in length, 4 cm in length, 2 cm in length, 1 cm in length, 8 mm in length, 6 mm in length, or 4 mm in length.

Prior to implantation, surgical procedures are performed to prepare the intervertebral space between adjacent vertebrae. The nucleus and annulus of the disc may be substantially removed, or a portion of the annulus may be retained to assist in retaining the implant and/or cement, which will be discussed below.

Generally, when the spinal fusion method includes a fusion device of the invention that does not have a flexible outer surface, the method includes removing the disc and preparing the endplates. The device is inserted into the prepared space, and the device can then be injected with cement as described herein.

In some methods of the invention, the superior and/or the inferior vertebral body endplates are initially prepared so as to permit the cement, which is injected into the fusion device of the invention, to interdigitate with endplate cortical bone and/or with cancellous bone of the vertebral body. The vertebral endplates may be prepared with scraper or rasp and may also be shaped to resist expulsion of the implant. The endplates are naturally cup-like having a natural concavity in both the lateral direction and the anterior-posterior direction. Preparation of the endplates may include providing a desired contour to the vertebral surfaces within the intervertebral space; roughening and violating the vertebral surfaces to induce bleeding; and can include sufficiently thinning the endplates to permit permeation of blood through the endplates.

Preferably, the endplates are thinned by removing about 0.5 to about 3 mm of the endplate to induce bleeding through the endplates. Inducing vertebral bleeding promotes bone growth from the vertebrae and between the fusion device and the vertebrae. The endplates may also be prepared by perforating the endplates to facilitate interdigitation of the endplates with cement. Preferably, the perforated endplates include holes in the range of about 10 microns to about 5 mm in diameter with a perforation density of at least 10%, 20%, 30%, 40%, 50%, 60%, 70%, or 80% or more.

The surgeon's decision whether to remove substantially all of the endplate or retaining the cortical bone will largely be dictated by the quality of the cancellous bone in the vertebrae. In certain instances, it may be desirable to retain substantially the entire endplate facing surface so that the implant body itself does not penetrate appreciably into the cancellous bone of the adjacent vertebral bodies. For example, the endplates should be substantially maintained for an osteoporotic patient. In other instances, it may be desirable to remove at least 10%, 20%, 40%, 60%, or 80% of endplate to expose the underlying cancellous bone. For example, a patient with denser cancellous bone in the vertebrae (i.e. non-osteoporotic as measured by DEXA scan) can better tolerate the removal of the endplates. Exposure of the underlying cancellous bone will allow for more extensive interdigitation of the cement and a more stable vertebral motion segment.

A fusion implant device according to the invention is then inserted between the prepared superior and inferior bodies. If the device includes a graft compartment, the method further includes placing bone graft material into the graft compartment. Once the implant and graft material are implanted within the intervertebral space, closely-matched contours between upper and lower contacting surfaces reduce the likelihood of bone subsidence around the implant by distributing compressive forces across the upper and lower endplate facing surfaces. A sufficient amount of cement is injected into the device so that the cement (a) fills the one or more hollow cores of the device and (b) permeates from the one or more hollow cores, contacts and, preferably, interdigitates with the prepared endplate cortical bone and/or cancellous bone.

When the endplates have been prepared, preferably a sufficient amount of cement is injected into the fusion device so that a portion of the cement exits the fusion device to infiltrate the cancellous region of the adjacent vertebral bodies. More preferably, cement is injected to infiltrate the cancellous region of the disc to a predetermined extent, which is less than about 30 mm into the cancellous region of the disc space, even more preferably less than about 20 mm, less than about 10 mm, less than about 8 mm, less than about 6 mm, less than about 5 mm, less than about 4 mm, less than about 3 mm, less than about 2 mm, or less than about 1 mm into the cancellous bone. Cement injection can be stopped once the suitable amount of cement has infiltrated into the cancellous region of the disc to the predetermined extent.

Preferably, the volume of cement injected into the implant and bone is less than about 200 ml, more preferably less than about 175 ml, 150 ml, 100 ml, 75 ml, 50 ml, 25 ml, 15 ml, 10 ml or 5 ml.

Cement injection can be conducted with a maximum pressure of 150 psi, 125 psi, 100 psi, 75 psi, 50 psi, 25 psi, 10 psi or 5 psi or less. Cement injection should Once the cement has set, independent motion of the fused vertebrae is substantially or wholly eliminated without the need for adjuvant fixation, such as attachment of plates or rods, or drilling, tapping, or insertion of screws.

The outlet opening of the accumulation chamber is preferably maximized in size so that the cement material discharged therethrough is distributed over a large surface area along the facing vertebral surface. In a preferred form, the accumulation chamber can be an open ended chamber either at one or both of its axial ends so that the outlet opening thereof is the same size as the remainder of the chamber. For instance, with a chamber having a circular periphery in the implant body, the diameter of the chamber can be constant between the axial ends thereof including at the opening at one of the ends thereof. In this manner, the flow path for the cement including the narrow fill channel portion and the enlarged axially extending accumulation chamber is operable to fill and reinforce essentially the entire chamber of the implant body with settable cement and also to conduct the preferred rapid-setting cement composition to vertebral surfaces adjacent the chamber, fixing the vertebral surfaces and implant body together with cement material.

In another method, a spinal fusion device of the invention made of flexible materials is inserted between a superior and an inferior vertebral body using a minimally invasive percutaneous procedure, for example, through a cannula. Generally, when a fusion implant is to be inserted, the disc is removed and the endplates are prepared as described above. When a flexible implant is to be inserted, the entire disc or the disc nucleus are removed and the endplates prepared, as described above. Moreover, due to the device's flexible material, the procedure can include a relatively small incision and use endoscopic instrumentation. The flexible fusion device can be inserted into the prepared space using an instrument that holds the device while it is pushed through the cannula. When the fusion device that includes an outer surface made of flexible material is placed in the disc space, the device can be injected with a sufficient amount of cement so that the cements fills one or more hollow cores in the device and permeates from the superior and/or inferior portion of the surface and contacts the adjacent vertebral body surface. Once the cement is injected and, preferably, once the cement has set, the patient can be placed in a neutral position.

The percutaneous procedure to insert the flexible fusion device can be performed unguided or with surgical guidance, such as by fluoroscopy. Surgical guidance facilitates the determination of the suitable amount of cement to be injected. In these methods, cement is injected into the hollow cavity of the device, the cement then contacts both the superior and inferior endplates, which have been prepared to allow cement to infiltrate the cancellous bone region. Cement injection can be stopped once the suitable amount of cement has infiltrated into the cancellous region of the disc to a predetermined extent, for example, when cement has infiltrated less than about 1 mm into the cancellous region of the disc space, less than about 2 mm into the cancellous region of the disc space, less than about 3 mm into the cancellous region of the disc space, less than about 4 mm into the cancellous region of the disc space, less than about 5 mm into the cancellous region of the disc space, less than about 6 mm into the cancellous region of the disc space, less than about 8 mm into the cancellous region of the disc space, less than about 10 mm into the cancellous region of the disc space, less than about 20 mm into the cancellous region of the disc space or less than about 30 mm into the cancellous region of the disc space.

A suitable amount of cement for injection preferably includes a volume of less than about 1 ml, less than about 2 ml, less than about 3 ml, less than about 4 ml, less than about 5 ml, less than about 6 ml, less than about 8 ml, less than about 10 ml, less than about 15 ml, less than about 20 ml, less than about 25 ml, less than about 50 ml, less than about 75 ml, less than about 100 ml, less than about 125 ml, less than about 150 ml, less than about 175 ml. Cement injection can be conducted with a maximum pressure of about 150 psi, 125 psi, 100 psi, 75 psi, 50 psi, 25 psi, 10 psi or 5 psi or less. Once a suitable amount of cement has been injected, the patient should preferably not be moved for at least 5 minutes, for at least 10 minutes, for at least 15 minutes, for at least 20 minutes, for at least 25 minutes, or for at least 30 minutes to allow enough time for the cement to become at least partially set before the patient is moved.

Once the cement has set in the fusion device with and without the flexible wall, independent motion of the vertebrae is substantially or wholly eliminated. This can be confirmed with bench and ex-vivo biomechanical testing. The described spinal fusion procedure can be performed on a cadaver spine or synthetic vertebral analogues. Dissecting and retrieving only the device and the bone interdigitated with cement, this construct can be tested according to the standards set forth in ASTM F-2077 (Test Methods For Intervertebral Body Fusion Devices) published by ASTM International (West Conshohocken, Pa.). In preferred embodiments, testing will demonstrate that the device/tissue construct has a fatigue life of at least about 500,000, 1,000,000, 1,500,000, 2,000,000, 2,500,000, 3,000,000, 3,500,000, 4,000,000, 5,000,000, 7,500,000, 10,000,000, 15,000,000, 20,000,000, or 25,000,000 cycles under the following loads. For compressive loads, at least about 50 N, 100 N, 200 N, 300 N, 400 N, 500 N, 750 N, 1000 N, 1250 N, 1500 N, 1750 N, 2000 N, 2500 N, 3500 N, 4000 N, 5000 N, or 10,000 N. For torsionals loads, at least about 0.25 N-m, 0.5 N-m, 0.75 N-m, 1 N-m, 1.25 N-m, 1.5 N-m, 1.75 N-m, 2 N-m, 2.25 N-m, 2.5 N-m, 2.75 N-m, 3 N-m, 3.5 N-m, 4 N-m, 4.5 N-m, 5 N-m, 6 N-m, 8 N-m, or 10 N-m with a combined compressive load of at least about 5 N, 50 N, 100 N, 200 N, 300 N, 400 N, 500 N, 750 N, 1000 N, 1250 N, 1500 N, 1750 N, 2000 N, 2500 N, 3500 N, 4000 N, 5000 N, 10,000 N. For shear loads, at least about 50 N, 100 N, 200 N, 300 N, 400 N, 500 N, 750 N, 1000 N, 1250 N, 1500 N, 1750 N, 2000 N, 2500 N, 3500 N, 4000 N, or 5000 N.

In addition, ex-vivo range of motion testing can be used to evaluate the fusion device of the invention (or a system that includes the device). The device can be inserted between two adjacent vertebral bodies in a cadaver spine or implanted in a live animal spine for 1 month, 2 months, 3 months, 6 months, 12 months or 24 months. The stiffness of the device-tissue motion segment can be tested using the following general method, developed by McAfee, et. al., "Cervical disc replacement-porous coated motion prosthesis: a comparative biomechanical analysis showing the key role of the posterior longitudinal ligament," *Spine* 15; 28(20):S176-85 (2003). The vertebral motion segment is cleaned of residual musculature with care taken to preserve all ligamentous attachments and operative motion site integrity. The cephalad and caudal ends of each specimen are secured in mounts, and plexiglass motion detection markers are placed on the specimen. Each marker is equipped with three non-co-linear light emitting diodes designed for detection by an optoelectronic motion measurement system (3020 OptoTrak System). To determine the multidirectional flexibility properties, six pure, unconstrained moments: flexion and extension (±4 Nm X-axis), left and right lateral bending (±4 Nm Z-axis), and left and right torsion (±4 Nm Y-axis) are applied to the superior end of the vertically oriented specimen while the caudal portion of the specimen remained fixed to a testing platform. A maximum applied moment of ±4 Nm is used for each loading mode and applied at a ramp rate of 3 degrees/second using a six degree of freedom spine simulator (6DOF-SS). A total of three load/unload cycles are performed for each motion with data analysis based on the final cycle. For the six main motions—corresponding to the moments applied—the operative level vertebral rotations (degrees) are quantified in terms of peak range of motion (ROM) and neutral zone (NZ). Peak ROM is defined as the peak displacement from the initial neutral position to maximum load, while neutral zone NZ represents the motion from the initial neutral position to the unloaded position at the beginning of the third cycle.

When preferred embodiments of the device or systems of the invention are implanted and tested according to the foregoing ex-vivo range-of-motion test, the preferred embodiments feature a ROM for flexion and extension, left and right lateral bending and left and right torsion will be no more than 10 degrees, 8 degrees, 7 degrees, 6 degrees, 5 degrees, 4 degrees, 3 degrees, 2 degrees, 1 degree.

After the fusion device and cement have been implanted for 6, 12 and 18 months, the device and the bone interdigitated with cement, this construct can be tested according to the standards set forth in ASTM F-2077, which can include testing in sheep or goat models for cervical or lumbar spinal fusion. In preferred embodiments, testing will demonstrate that the device/tissue construct has a fatigue life after 6, 12, or 18 months of implantation of at least about 500,000, 1,000,000, 1,500,000, 2,000,000, 2,500,000, 3,000,000, 3,500,000, 4,000,000, 5,000,000, 7,500,000, 10,000,000, 15,000,000, 20,000,000, 25,000,000 cycles under the following loads. For compressive loads, at least about 50 N, 100 N, 200 N, 300 N, 400 N, 500 N, 750 N, 1000 N, 1250 N, 1500 N, 1750 N, 2000 N, 2500 N, 3500 N, 4000 N, 5000 N, or 10,000 N. For torsionals loads, at least about 0.25 N-m, 0.50 N-m, 0.75 N-m, 1.00 N-m, 1.25 N-m, 1.50 N-m, 1.75 N-m, 2.00 N-m, 2.25 N-m, 2.50 N-m, 2.75 N-m, 3.00 N-m, 3.50 N-m, 4.00 N-m, 4.50 N-m, 5.00 N-m, 6.00 N-m, 8.00 N-m, or 10.00 N-m with a combined compressive load of at least about 5 N, 50 N, 100 N, 200 N, 300 N, 400 N, 500 N, 750 N, 1000 N, 1250 N, 1500 N, 1750 N, 2000 N, 2500 N, 3500 N, 4000 N, 5000 N, or 10,000 N. For shear loads, at least about 50 N, 100 N, 200 N, 300 N, 400 N, 500 N, 750 N, 1000 N, 1250 N, 1500 N, 1750 N, 2000 N, 2500 N, 3500 N, 4000 N, or 5000 N.

After the fusion device and cement have been implanted for 6, 12 and 18 months, the range of motion as tested according to the foregoing ex-vivo range-of-motion test, the preferred embodiments feature a ROM for flexion and extension, left and right lateral bending and left and right torsion will be no more than about 10 degrees, 8 degrees, 7 degrees, 6 degrees, 5 degrees, 4 degrees, 3 degrees, 2 degrees, or 1 degree.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A flexible fusion device comprising:
   a flexible outer surface including upper and lower vertebral body engaging surfaces for respectively engaging with upper and lower vertebral bodies;
   at least a portion of one of the upper and lower vertebral body engaging surfaces that is configured to be cement permeable;
   a sidewall extending between the upper and lower vertebral body engaging surfaces with the entirety of the sidewall being configured to be impermeable to cement; and
   a hollow core about which the flexible outer surface extends;
   wherein the flexible outer surface is configured for insertion between the upper and lower vertebral bodies and the hollow core is configured to direct the flow of cement injected into the hollow core through the cement permeable portion of at least one of the upper and lower vertebral body engaging surfaces and into contact with the corresponding one of the upper and lower vertebral bodies;
   wherein the hollow core comprises a first hollow core for receiving cement and a second hollow core for receiving cement with both the first and second hollow cores having the outer surface extending thereabout; and a midsection wall separating the first and second hollow cores and configured to be impermeable to cement, wherein the first hollow core is configured such that cement injected therein will flow through the cement permeable portion of the upper vertebral body engaging surface to contact the upper vertebral body, and the second hollow core is configured such that cement injected therein will flow through the cement permeable portion of the lower vertebral body engaging surface to contact the lower vertebral body.

2. The fusion device of claim 1 further comprising an injection port in the outer surface for injecting cement into at least one of the hollow cores.

3. The fusion device of claim 1, further comprising a graft compartment configured for holding bone graft material having the outer surface extending thereabout, the graft compartment being separated from the first and second hollow cores by a cement impermeable wall.

4. The fusion device of claim 1, wherein the upper and lower vertebral body engaging surfaces each have a portion that bounds a portion of the core and a portion that bounds a portion of the graft compartment, and the portions of the upper and lower vertebral body engaging surfaces that bound the core portion are cement permeable and have a permeability that differs from the permeability of the portions of the upper and lower vertebral body engaging surfaces which bound the graft compartment portion.

5. The fusion device of claim 1, wherein the sidewall has an arcuate configuration.

6. The fusion device of claim 1, wherein the cement permeable portion of the one of the upper and lower vertebral body engaging surfaces includes a plurality of pores or openings.

7. The fusion device of claim 1, wherein the outer surface is of a woven or mesh material.

8. The fusion device of claim 7, wherein the cement permeable portion of at least one of the upper and lower vertebral body engaging surfaces has a looser weave or mesh than the sidewall extending between the upper and lower vertebral body engaging surfaces which has a relatively denser weave or finer mesh that is impermeable to cement.

9. The fusion device of claim 1, wherein the outer surface, including the upper and lower vertebral body engaging surfaces and the sidewall extending therebetween form a disc-shaped device.

10. The fusion device of claim 1, wherein the sidewall comprises a cement barrier sheet configured to render the sidewall impermeable to cement.

11. The fusion device of claim 1, wherein the hollow core has a ring shape that extends about a centrally located graft compartment.

12. A spinal fusion system comprising:
the fusion device of claim 1; and
a suitable amount of cement or cement components that, when mixed, form a suitable amount of cement;
wherein the suitable amount of cement comprises enough to fill at least one of the first and second hollow cores of the fusion device and contact the upper vertebral body; the lower vertebral body; or both the upper and the lower vertebral bodies.

13. The spinal fusion system of claim 12, wherein:
the suitable amount of cement comprises enough to contact both the upper and the lower vertebral bodies.

14. The spinal fusion system of claim 12, wherein the cement is, or the cement components, when mixed, form, a polymethylmethacrylate (PMMA) cement, calcium phosphate cement, or a composite cement thereof consisting of a polymer or epoxy in combination with a calcium phosphate filler.

15. The spinal fusion system of claim 12, wherein the cement is, or the cement components, when mixed, form, a composite cement, and the composite cement comprises one or more fillers selected from the group consisting of glass, bone, calcium phosphate, and glass ionomer cements.

16. The spinal fusion system of claim 12, wherein the cement is formed from components comprising or the cement components comprise (i) a first component comprising a polymerizable resin that includes an ethylenic unsaturated double bond; and (ii) a second component comprising a compound that includes more than one type of amine selected from the group consisting of a primary amine, a secondary amine, a tertiary amine, and a quaternary amine, and wherein the first component and second component are capable of reacting with each other in a polymerization reaction.

17. The spinal fusion system of claim 12, wherein the cement is formed from components comprising or the cement components comprise (i) a first component that includes at least one glycidyl group, and, optionally, at least one ester or carbonate group and (ii) a second component that includes polyethyleneimine (PEI) or a derivative thereof.

18. The spinal fusion system of claim 12, wherein the system is free of additional stabilizing appliances.

19. A spinal fusion method comprising
inserting the spinal fusion device of claim 1 between the upper and lower vertebral body of a subject in need of spinal fusion; and
injecting a suitable amount of cement into at least one of the first and second hollow cores;
wherein the suitable amount of cement comprises enough to (a) fill at least one of the first and second hollow cores of the fusion device and (b) contact the upper vertebral body, the lower vertebral body, or both the upper and the lower vertebral bodies.

20. The spinal fusion method of claim 19; wherein
the suitable amount of cement comprises enough to contact both the upper and the lower vertebral bodies.

21. The spinal fusion method of claim 19; wherein the device is inserted by a minimally invasive procedure.

22. The spinal fusion method of claim 19; wherein the spinal fusion device comprises a graft compartment and the method further includes adding bone graft material.

23. The spinal fusion method of claim 19; wherein the subject has a spinal condition selected from the group consisting of a fractured vertebra, spondylolisthesis, protrusion or degeneration of the spinal disc, abnormal curvature of the spine (such as scoliosis or kyphosis), spinal tumor, spinal infection, or spinal instability.

24. The spinal fusion method of claim 19; wherein the cement is or the cement components, when mixed, form, a composite cement, and the composite cement comprises one or more fillers selected from the group consisting of glass, bone, calcium phosphate, and glass ionomer cements.

25. The spinal fusion method of claim 19; wherein the fusion procedure is completed without attaching an additional stabilizing appliances to the upper and lower vertebral body.

26. The spinal fusion method of claim 19; wherein the method further comprises attaching one or more additional stabilizing appliances to the subject's spine.

* * * * *